(12) United States Patent
Singh et al.

(10) Patent No.: US 8,173,818 B2
(45) Date of Patent: May 8, 2012

(54) PROCESS FOR PRODUCING SULPHOXIDE COMPOUNDS

(75) Inventors: Anand Singh, Distt Jaunpur (IN);
Khushwant Singh, Ambala Cantt (IN);
Sushil Kumar Dubey, Noida (IN)

(73) Assignee: Jubilant Organosys Limited, Noida (IN)

( * ) Notice: Subject to any disclaimer, the term of this patent is extended or adjusted under 35 U.S.C. 154(b) by 562 days.

(21) Appl. No.: 12/376,631

(22) PCT Filed: Aug. 8, 2007

(86) PCT No.: PCT/IN2007/000335
§ 371 (c)(1),
(2), (4) Date: Feb. 25, 2009

(87) PCT Pub. No.: WO2008/018091
PCT Pub. Date: Feb. 14, 2008

(65) Prior Publication Data
US 2010/0179328 A1 Jul. 15, 2010

(30) Foreign Application Priority Data
Aug. 8, 2006 (IN) .......................... 1796/DEL/2006

(51) Int. Cl.
*C07D 401/12* (2006.01)
(52) U.S. Cl. .............. 546/273.7; 546/277.7; 548/306.4
(58) Field of Classification Search ............... 546/273.7, 546/277.7; 548/306.4
See application file for complete search history.

(56) References Cited
U.S. PATENT DOCUMENTS
7,301,030 B2 * 11/2007 Kohl et al. ................. 546/273.7

FOREIGN PATENT DOCUMENTS
| WO | WO 96/02535 A1 | 2/1996 |
| WO | WO 2004/052882 A1 | 6/2004 |
| WO | WO 2006/040635 A1 | 4/2006 |
| WO | WO 2007/088559 A1 | 8/2007 |

OTHER PUBLICATIONS

Bonchio et al., "The First Chiral, etc.," J. Org. Chem., 64(4) pp. 1326-1330, (1999).*
Hanna Cotton, et al. "Asymmetric Synthesis of Esomeprazole", Tetrahedron: Asymmetry, XP002942435, vol. 11, 2000, pp. 3819-3825.

* cited by examiner

*Primary Examiner* — Patricia Morris
(74) *Attorney, Agent, or Firm* — Oblon, Spivak, McClelland, Maier & Neustadt, L.L.P.

(57) ABSTRACT

Disclosed herein, a process for producing sulphoxide compound of the Formula (I) by asymmetrically oxidizing a prochiral sulphide of the Formula (II) with an effective amount of oxidizing agent in the presence of a chiral transition metal complex without using an organic solvent and base.

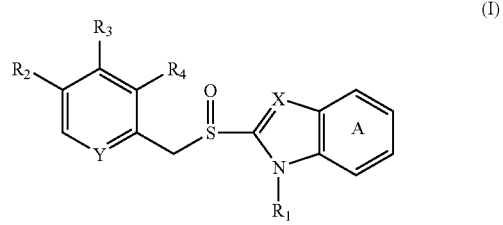

(I)

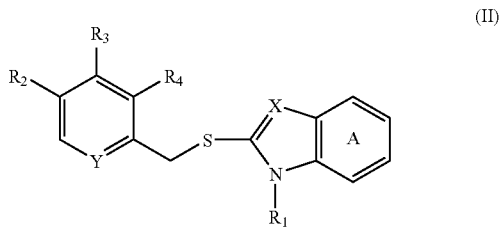

(II)

24 Claims, No Drawings

PROCESS FOR PRODUCING SULPHOXIDE COMPOUNDS

FIELD OF THE INVENTION

This invention, in general relates to an improved process for producing sulphoxide compounds. In more particularly, the present invention provides an improved process for producing sulphoxide compounds either as a single enantiomer or in an enantiomerically enriched form by asymmetrically oxidizing a prochiral sulphide with an oxidizing agent in the presence of a chiral transition metal complex without using an organic solvent and base.

BACKGROUND OF THE INVENTION

Substituted 2-(2-pyridinylmethyl sulphinyl)-1H-benzimidazoles such as omeprazole, lansoprazole, pantoprazole and rabeprazole are known as gastric acid secretion inhibitors. Omeprazole, chemically known as 5-methoxy-2-[(4-methoxy-3,5-dimethyl-2-pyridinyl)methylsulphinyl-1H-benzimidazole) which is useful as an antiulcer agent.

These structurally related sulphoxide compounds have a stereogenic center at the sulphur atom and thus exist as enantiomers.

There are several methods known in the prior art, which discloses the asymmetric oxidation of prochiral sulfide.

U.S. Pat. No. 5,948,789 and Eur. J. Biochem., 166 (1987), 453, describes enantioselective synthesis of substituted sulphoxide. In this process, a prochiral sulphide is oxidized into the corresponding sulphoxide either as a single enantiomer or in an enantiomerically enriched form using oxidizing agent in the presence of chiral titanium complex and in presence of base and organic solvent.

Similarly, WO2003089408 describes an enantioselective catalytic oxidation of sulfide with an oxidizing agent in an organic solvent and base and in the presence of titanium or vanadium complex with a chiral monodentate ligand.

WO2005054228 describes an enantioselective process for the preparation of substituted benzimidazole by asymmetrically oxidizing substituted prochiral sulphide preferably halo or nitro substituted, in an organic solvent and base with an oxidizing agent and a chiral titanium complex into the corresponding sulphoxide.

WO2005080374 describes enantioselective synthesis of sulphoxide compound either as a single enantiomer or in an enantiomerically enriched form by oxidizing prochiral sulphoxide, with an oxidizing agent in an organic solvent at a temperature between 20-40° C. and in the presence of chiral titanium complex.

WO2006040635 describes synthesis of substituted sulphoxide by oxidizing prochiral sulphoxide in presence of chiral titanium metal complex and a base in the absence of an organic solvent.

The above mentioned prior art references discloses the process of oxidation which is costly and not an environmental friendly. The other disadvantage is requirement of strict reaction condition during the oxidation and formation of sulphone by-product, makes the process industrially uneconomical.

Therefore, there is an increasing need for developing an economically viable and eco-friendly process for the preparation of sulphoxide either as a single enantiomer or in an enantiomerically enriched form, which avoids the use of organic solvent and base, the product is free from sulfone by-product and the process of preparation should to be cost effective and high yielding.

OBJECTS AND SUMMARY OF THE INVENTION

It is a principal object of the present invention to provide an economically viable and eco-friendly process for producing sulphoxide compounds either as a single enantiomer or in an enantiomerically enriched form, which obviates the drawbacks associated with the prior arts.

Another object of the present invention is to provide an improved process for producing sulphoxide compounds either as a single enantiomer or in an enantiomerically enriched forth, which involves simple and economical chemical steps by avoiding the use of organic solvent and base.

It is yet another object of the present invention is to provide a process for producing optically pure sulphoxide compounds either as a single enantiomer or in an enantiomerically enriched form, wherein the process avoids the production of by products.

The above and other objects are attained in accordance with the present invention wherein there is provided following embodiments, however the described embodiments hereinafter is in accordance with the best mode of practice and the invention is not restricted to the particular embodiments.

In accordance with one preferred embodiment of the present invention, there is provided a process for producing sulphoxide compounds of Formula I either as a single enantiomer or in an enantiomerically enriched form, the process comprises of asymmetrically oxidizing a prochiral sulphide of Formula II with an oxidizing agent in the presence of a chiral transition metal complex, wherein the reaction is carried out in absence of organic solvent and base.

In accordance with another preferred embodiment of the present invention, there is provided a process for producing sulphoxide compounds of Formula I either as a single enantiomer or in an enantiomerically enriched form, wherein the process comprises of asymmetrically oxidizing a prochiral sulphide of Formula II with a selective amount of oxidizing agent in the presence of a chiral transition metal complex, thereby avoiding the formation of by-products such as sulfone.

In accordance with one other preferred embodiment of the present invention, there is provided a process for producing sulphoxide compounds of Formula I either as a single enantiomer or in an enantiomerically enriched form, the process comprises of asymmetrically oxidizing a prochiral sulphide of Formula II with a selective amount of oxidizing agent in the presence of a chiral transition metal complex without using organic solvent and base, and converting the resultant into a pharmaceutically acceptable salt employing an alkali and/or alkaline earth metal source.

In accordance with another preferred embodiment of the present invention, there is provided a process for producing sulphoxide compounds of Formula I either as a single enantiomer or in an enantiomerically enriched form, the process comprises of asymmetrically oxidizing a prochiral sulphide of Formula II with a selective amount of oxidizing agent in the presence of a chiral transition metal complex, wherein the oxidizing agent used in the process is about 1.1 to 1.4 molar equivalents relative to the compound of the Formula II.

In accordance with yet another preferred embodiment of the present invention, there is provided a process for producing sulphoxide compound of Formula I either as a single enantiomer or in an enantiomerically enriched form, the process comprises of asymmetrically oxidizing a prochiral sulphide of Formula II with a selective amount of oxidizing agent in the presence of a chiral transition metal complex without using organic solvent and base, converting the resultant into a salt employing an alkali and/or alkaline earth metal source. The resulting alkali or alkaline earth metal salts of the optically active substituted sulphoxide compound of the Formula [1] is further converted to another pharmaceutical acceptable alkali or alkaline earth metal salts.

In accordance with yet another preferred embodiment of the present invention there is provided a process for producing sulphoxide compounds of Formula I either as a single enantiomer or in an enantiomerically enriched form, wherein the process discussed above is carried out in the presence of a catalyst.

DETAIL DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The disclosed embodiment of the present invention provides a cost effective and industrial feasible process for the production of sulphoxide compounds wherein said process comprises of asymmetrically oxidizing a prochiral sulphide of Formula II with a selective amount of oxidizing agent in the presence of a chiral transition metal complex without using organic solvent and base, converting the resultant into a salt. The resulting alkali or alkaline earth metal salts of the optically active substituted sulphoxide compound of the Formula [1] is further converted to another pharmaceutical acceptable alkali or alkaline earth metal salts.

The present invention discloses a process for producing sulphoxide compounds of Formula I either as a single enantiomer or in an enantiomerically enriched form,

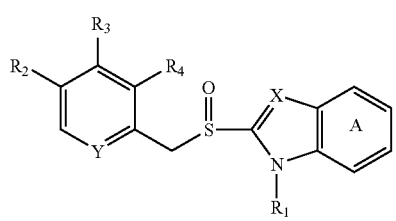

Formula I wherein
ring A is a benzene ring optionally having 1 to 3 substituent (s) selected from (a) a halogen atom, (b) a cyano, (c) a nitro, (d) a $C_{1-7}$ alkyl optionally having 1 to 3 substituent(s) selected from a halogen atom, a hydroxy, a $C_{1-6}$ alkoxy- a $C_{1-6}$ alkoxycarbonyl and carbamoyl, (e) a hydroxy, a $C_{1-6}$ alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) a $C_{6-14}$ aryl (h) a $C_{6-14}$ aryloxy (i) a carboxy (j) an acyl selected from formyl a $C_{1-6}$ alkyl-carbonyl, a $C_{1-6}$ alkoxy-carbonyl, a carbamoyl, an N—$C_{1-6}$ alkyl an N,N-di $C_{1-6}$ alkyl-carbamoyl, a $C_{1-7}$ alkylsulfinyl and a $C_{1-7}$ alkylsulfonyl, (k) an acyloxy selected from a $C_{1-6}$ alkyl-carbonyloxy, a $C_{1-6}$ alkoxy-carbonyloxy, a carbamoyloxy, a $C_{1-6}$ alkyl-carbamoyloxy, a $C_{1-7}$ alkylsulfinyloxy and a $C_{1-7}$ alkylsulfonyloxy and (l) a 5- to 10-membered heterocyclic group, $R_1$ is a hydrogen atom, or a group selected from (A) a $C_{1-6}$ alkyl group, a $C_{3-14}$ cycloalkyl group, a $C_{2-6}$ alkenyl group, a $C_{3-14}$ cycloalkenyl group and a $C_{2-6}$ alkynyl group, each of which optionally has 1 to 3 substituent(s) selected from (a) a $C_{1-4}$ alkylthio group, (b) a halogen, (c) a $C_{1-6}$ alkoxy group,
(d) an acyloxy group selected from a $C_{1-6}$ alkyl-carbonyloxy group, a $C_{1-6}$ alkoxy-carbonyloxy group, a $C_{1-6}$ alkyl-carbamoyloxy group, a $C_{1-7}$ alkylsulfinyloxy, a $C_{1-7}$ alkylsulfonyloxy and a $C_{6-14}$ aryl-carbonyloxy group, (e) a nitro group, (f) a $C_{1-6}$ alkoxy-carbonyl group, (g) a mono- or di-$C_{1-6}$ alkylamino group, (h) a $C_{1-6}$ alkoxyimino group and (i) a hydroxyimino (B) a $C_{6-14}$ aryl group and a $C_{7-19}$ aralkyl group, each of which optionally has 1 to 5 substituent (s) selected from (a) a $C_{1-6}$ alkyl group, (b) a $C_{3-6}$ cycloalkyl group, (c) a $C_{2-6}$ alkenyl group, (d) a $C_{2-6}$ alkynyl group, (e) a $C_{1-6}$ alkoxy group, (f) an acyl group selected from $C_{1-7}$ alkanoyl, a $C_{6-14}$ aryl-carbonyl, a $C_{1-6}$ alkoxy-carbonyl, a $C_{6-14}$ aryloxy-carbonyl, a $C_{7-19}$ aralkyl-carbonyl and a $C_{7-19}$ aralkyloxycarbonyl, (g) a nitro, (h) an amino, (i) a hydroxy, (j) a cyano, (k) a sulfamoyl, (l) a mercapto, (m) a halogen and (n) a $C_{1-4}$ alkylthio (C) an acyl group selected from formyl, a $C_{1-6}$ alkyl-carbonyl, a $C_{1-6}$ alkoxy-carbonyl, a carbamoyl, an N—$C_{1-6}$ alkyl-carbamoyl, an N,N-di-$C_{1-6}$ alkyl-carbamoyl, a $C_{1-7}$ alkylsulfinyl and a $C_{1-7}$. allylsulfonyl and (D) an acyloxy group selected from a $C_{1-6}$ alkyl-carbonyloxy, a $C_{1-6}$ alkoxy-carbonyloxy, a carbamoyloxy, a $C_{1-6}$ alkyl-carbamoyloxy, a $C_{1-7}$ alkylsulfinyloxy and a $C_{1-7}$ alkylsulfanyloxy, $R_2$, $R_3$ and $R_4$ are each a hydrogen atom, a $C_{1-7}$ alkyl group optionally having 1 to 3 substituent(s) selected from a halogen atom, a hydroxy, a $C_{1-6}$ alkoxy, a $C_{1-6}$ alkoxy-carbonyl and a carbamoyl; a $C_{1-6}$ alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino group; a mono-$C_{1-6}$ alkylamino; a mono-$C_{6-14}$ arylamino; a di-$C_{1-6}$ alkylamino, or a di-$C_{6-14}$ arylamino,
X is a nitrogen atom or CH,
Y is a nitrogen atom or CH,
by asymmetrically oxidizing a prochiral sulphide of the Formula II

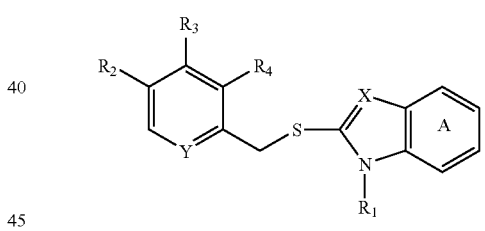

Formula II wherein the $R_1$, $R_2$, $R_3$, $R_4$, are as defined above, with an oxidizing agent in the presence of a chiral transition metal complex without using organic solvent and base.

The prochiral sulfide of the Formula II is prepared by various methods known in the art. The prochiral sulfide of The Formula II is obtained as a solution for example from a reaction mixture resulting directly from a reaction in which it is formed.

According to the present invention, the asymmetric oxidation is carried out in the presence of oxidizing agent selected from hydrogen peroxide, alkyl hydroperoxide, arylalkyl hydroperoxide or mixtures thereof. Preferably the oxidizing agents used in the process are selected from tertiary butyl hydroperoxide and cumene hydroperoxide and the like. The amount of the oxidizing agent to be used is about 1.1 to 1.4 molar equivalents relative to the compound of the Formula II.

Further, the asymmetric oxidation is carried out in the presence of chiral transition metal complex, which is prepared from a transition metal compound and a chiral ligand. The transition metal is selected from the group comprising titanium, vanadium, molybdenum and tungsten, preferably titanium, vanadium and tungsten compound. Preferred transition metal compound is titanium (IV) isopropoxide, titanium (IV) propoxide, titanium (IV) ethoxide, titanium (N) methoxide, vanadium oxy tripropoxide or vanadium oxytriisopropoxide and the like. The chiral transition metal complex is prepared in the presence of prochiral sulphide or before the prochiral sulphide is added to the reaction vessel.

The chiral ligand used herewith is selected from branched or unbranched alkyl diol or an aromatic diol. Preferred chiral diols are esters of tartaric acid especially (+)-diethyl L-tartarate or (−)-diethyl D-tartarate, (+)-dimethyl L-tartarate or (−)-dimethyl D-tartarate and the like.

The asymmetric oxidation is carried out at a temperature in the range of −20 to 25° C., preferably between −10 to 20° C. more preferably between 5-10° C. for a period of about 1-5 hours, preferably between 2-4 hours under inert atmosphere.

The asymmetric oxidation is carried out in presence of a catalyst. The preferred catalyst used in the process is water. The amount of water used in the complex is about 0.1 to 1.0 equivalents preferably about 0.3 to 0.6 equivalents relative to prochiral sulfide of Formula II.

The reaction is carried out under an inert atmosphere or under the inert gas stream. Examples of the inert gas include nitrogen, helium, neon, argon and the like.

The resulting sulphoxide compounds of Formula I prepared according to the present invention is further converted into optically active alkali and/or alkaline earth metal salt of sulphoxide by treating the optically active sulphoxide compound of Formula I, obtained by asymmetric oxidation of prochiral sulfide compound of Formula II, with an alkali and/or alkaline earth metal source. The alkali or alkaline earth metal source may be selected from $Na^+$, $Li^+$, $Mg^{+2}$, $Ca^{+2}$ and $Ba^{+2}$ salts such as bicarbonates, carbonates, hydrides, hydroxides, halides, sulphates, and oxides, preferably sodium hydroxide, potassium hydroxide, barium hydroxide, lithium hydroxide, magnesium hydroxide, calcium halide, magnesium halide and barium halide may be used.

The process of the present invention further includes the optional step of converting the resulting alkali or alkaline earth metal salts of the optically active sulphoxide compound of Formula I to another alkali or alkaline earth metal salts of these compounds. For example, S-omeprazole potassium is converted into S-omeprazole magnesium, wherein the alkali or alkaline earth metal source may be selected from $Na^+$, $Li^+$, $Mg^{+2}$, $Ca^{+2}$ and $Ba^{+2}$ salts such as bicarbonates, carbonates, hydrides, hydroxides, halides, sulphates, and oxides, preferably sodium hydroxide, potassium hydroxide, barium hydroxide, lithium hydroxide, magnesium hydroxide, calcium halide, magnesium halide and barium halide may be used.

The examples that follow are not intended to limit the scope of the invention as defined hereinabove or as claimed below:

Example 1

Preparation of 5-methoxy-2-[[(4-methoxy-3,5-dimethyl-2-pyridinyl)-methyl]sulfinyl]-1H-benzimidazole potassium salt Titanium isopropoxide (60.4.g) and D-(−) diethyl tartarate (87.6 g) was taken and stirred at room temperature under an inert atmosphere. Temperature was increased up to 55-60° C. and 5-methoxy-2-[(4-methoxy-3,5-dimethyl-2-pyridinyl)-methyl]thio]-1H-benzimidazole (100 g) was added at the above temperature. The resulting mixture was stirred for 30 minutes at the same temperature. Water (1.4 ml) was added and was stirred for another one hour. The resulting reaction mass was cooled to 5-10° C. and cumene hydroperoxide (78 g) was added. The resulting mixture was stirred for 3-4 hours at 5-10° C. After completion of the reaction, toluene, triethylamine and water was added to the resulting reaction mixture. The organic layer was separated and washed with water. The organic layer was then cooled to 10-15° C. and methanolic potassium hydroxide (17.9 g dissolved in 145 ml methanol) was added. The resulting mixture was stirred for 30 minutes, seeded with pure potassium S-omeprazole and further stirred for 3-4 hours at room temperature. The resulting solid was filtered off, washed with toluene and methanol and dried under vacuum for 2-3 hours at 45-50° C. The resulting solid was dissolved in water (350 ml) at room temperature. The pH was adjusted to 7.5-8.0 with acetic acid and dichloromethane (500 ml) was added. The organic layer was separated, washed with brine and distilled off. The resulting oily mass was dissolved in methyl ethyl ketone (350 ml) at room temperature under stirring. The resulting reaction mass was then cooled to 10-15° C. and methanolic potassium hydroxide (7.2 g potassium hydroxide in 36 ml methanol) was added. The resulting mixture was stirred for 4-5 hours at room temperature, first and then cooled to 10-15° C. under stirring. Solid was filtered off, washed with methyl ethyl ketone and dried under vacuum at 40-45° C. for 6-8 hours.

Yield:=45-50 g

Sulfone=0.15%

HPLC Purity=99.7%

Chiral purity=99.9%

Example 2

Preparation of 5-methoxy-2-[[(4-methoxy-3,5-dimethyl-2-pyridinyl)-methyl]sulfinyl]-1H-benzimidazole magnesium salt 5-methoxy-2-[[(4-methoxy-3,5-dimethyl-2-pyridinyl)-methyl]sulfinyl]-1H-benzimidazole potassium salt (100 g) was taken in water (500 ml) and was stirred at room temperature for 10-15 minutes. The pH was adjusted to 10-11 with acetic acid at and the mixture was stirred for half an hour 20-25° C. Methanol (100 ml) was added. Aqueous solution of magnesium chloride hexahydrate (20.3 g dissolved in 100 ml) was then added to the above mixture at room temperature under stirring. The mixture was stirred for 60 minutes at room temperature. The resulting solid was filtered, washed with methanol and water. The wet material was dried under reduced pressure at 40-45° C. for 8-10 hours.

Yield:=70-75 g

Sulfone=0.05%

HPLC Purity=99.5%.

Chiral purity=100%

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention.

We claim:
1. A process for producing sulphoxide compound of Formula I in an enantiomerically enriched form,

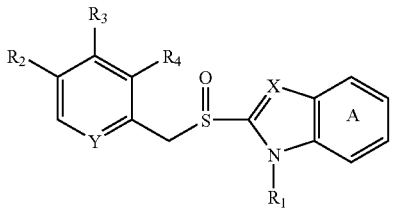

Formula I wherein
ring A is a benzene ring optionally having 1 to 3 substituent (s) selected from a $C_{1-6}$ alkoxy optionally having 1 to 3 substituent(s) selected from a halogen atom
$R_1$ is a hydrogen atom
$R_2$, $R_3$ and $R_4$ are each a hydrogen atom, a $C_{1-7}$ alkyl group; a $C_{1-6}$ alkoxy group optionally having 1 to 3 substituent(s) selected from a halogen atom, a $C_{1-6}$ alkoxy,
X is a nitrogen atom,
Y is a nitrogen atom
the process comprising:
asymmetrically oxidizing a prochiral sulphide of the Formula II;

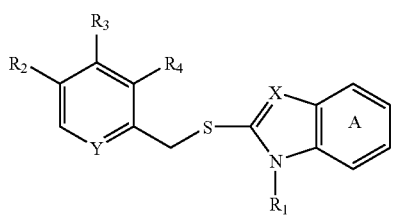

Formula II with an oxidizing agent and a chiral transition metal complex without using an organic solvent and base wherein said oxidizing agent is used in an amount of about 1.1 to 1.4 molar equivalents relative to said prochiral sulfide of the formula II and the chiral transition metal complex is prepared from a transition metal compound and a chiral ligand;
reacting the resultant compound of Formula I to prepare a salt employing an alkali and/or alkaline earth metal source,
wherein the $R_1$, $R_2$, $R_3$ and $R_4$, are as defined above.

2. The process according to claim 1, wherein the oxidizing agent is at least one oxidizing agent selected from alkyl hydroperoxide, aryl alkyl hydroperoxide or mixture thereof.

3. The process according to claim 1, wherein the transition metal is at least one metal selected from titanium, vanadium, molybdenum or tungsten.

4. The process according to claim 1, wherein the chiral ligand is at least one ligand selected from branched or unbranched alkyl diol or an aromatic diol.

5. The process according to claim 1, wherein the chiral ligand is a chiral ester of tartaric acid.

6. The process according to claim 1, wherein the chiral transition metal complex is prepared in the presence of prochiral sulphide or before the prochiral sulphide is added to the reaction vessel.

7. The process according to claim 1, wherein the alkali or alkaline earth metal source is at least one metal salt selected from $Na^+$, $Li^+$, $Mg^{+2}$, $Ca^{+2}$ and $Ba^{+2}$ salts of at least one of bicarbonates, carbonates, hydrides, hydroxides, halides, sulphates and oxides.

8. The process according to claim 1, wherein the asymmetric oxidation is carried out in presence of a catalyst.

9. The process according to claim 8, wherein the catalyst is water.

10. The process according to claim 9 wherein the amount of water is about 0.1 to 1.0 equivalents to prochiral sulfide of Formula II.

11. The process according to claim 1, wherein the resulting alkali or alkaline earth metal salts of the optically active sulphoxide compound of Formula I is further reacted with another pharmaceutically acceptable alkali or alkaline earth metal salts.

12. The process according to claim 11, wherein the alkali or alkaline earth metal source is at least one metal salt selected from $Na^+$, $Li^+$, $Mg^{+2}$, $Ca^{+2}$ and $Ba^{+2}$ salts of at least one of bicarbonates, carbonates, hydrides, hydroxides, halides, sulphates and oxides.

13. A process for producing sulphoxide compound of Formula I in an enantiomerically enriched form,

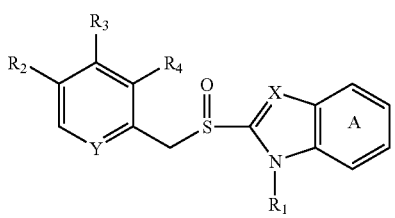

Formula I wherein
ring A is a benzene ring optionally having 1 to 3 substituent (s) selected from a $C_{1-6}$ alkoxy optionally having 1 to 3 substituent(s) selected from a halogen atom
$R_1$ is a hydrogen atom
$R_2$, $R_3$ and $R_4$ are each a hydrogen atom, a $C_{1-7}$ alkyl group a $C_{1-6}$ alkoxy group optionally having 1 to 3 substituent(s) selected from a halogen atom
X is a nitrogen atom,
Y is a nitrogen atom
the process comprising:
asymmetrically oxidizing a prochiral sulphide of the Formula II;

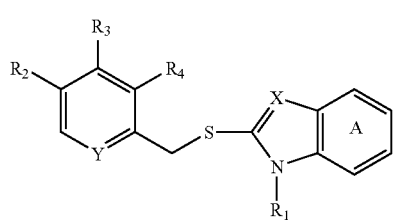

Formula II with an oxidizing agent and a chiral transition metal complex without using an organic solvent and base wherein said oxidizing agent is used in an amount of about 1.1 to 1.4 molar equivalents relative to said prochiral sulfide of the formula II and said chiral transition metal complex is prepared from a transition metal compound and a chiral ligand;

reacting the resultant compound of Formula I with an alkali and/or alkaline earth metal salt; and further reacting the resulting alkali or alkaline earth metal salts of the optically active sulphoxide compound of Formula I to prepare another pharmaceutical acceptable alkali or alkaline earth metal salts, wherein the $R_1$, $R_2$, $R_3$ and $R_4$, are as defined above.

14. The process according to claim 13, wherein the oxidizing agent is at least one oxidizing agent selected from alkyl hydroperoxide, aryl alkyl hydroperoxide or mixture thereof.

15. The process according to claim 13, wherein the transition metal is at least one metal selected from titanium, vanadium, molybdenum or tungsten.

16. The process according to claim 13, wherein the chiral ligand is at least one ligand selected from branched or unbranched alkyl diol or an aromatic diol.

17. The process according to claim 13, wherein the chiral ligand is a chiral ester of tartaric acid.

18. The process according to claim 13, wherein the chiral transition metal complex is prepared in the presence of prochiral sulphide or before the prochiral sulphide is added to the reaction vessel.

19. The process according to claim 13, wherein the asymmetric oxidation is carried out in presence of a catalyst.

20. The process according to claim 19, wherein the catalyst is water.

21. The process according to claim 20, wherein the amount of water is about 0.1 to 1.0 equivalents to prochiral sulfide of Formula II.

22. The process according to claim 13, wherein the alkali or alkaline earth metal source used in the process is at least one metal salt selected from $Na^+$, $Li^+$, $Mg^{+2}$, $Ca^{+2}$ and $Ba^{+2}$ salts of at least one of bicarbonates, carbonates, hydrides, hydroxides, halides, sulphates and oxides.

23. The process according to claim 1, wherein a single enantiomer is produced.

24. The process according to claim 13, wherein a single enantiomer is produced.

* * * * *